United States Patent [19]

Brink

[11] Patent Number: 5,725,560
[45] Date of Patent: Mar. 10, 1998

[54] DEFIBRILLATOR WITH WAVEFORM SELECTION CIRCUITRY

[75] Inventor: Gregory Dean Brink, McMinnville, Oreg.

[73] Assignee: Hewlett-Packard Company, Palo Alto, Calif.

[21] Appl. No.: 668,569

[22] Filed: Jun. 20, 1996

[51] Int. Cl.⁶ ................................................. A61N 1/39
[52] U.S. Cl. ............................................................ 607/5
[58] Field of Search ...................................... 607/5, 7, 8, 4

[56] References Cited

U.S. PATENT DOCUMENTS

| | | |
|---|---|---|
| 4,840,177 | 6/1989 | Charbonnier et al. . |
| 5,014,697 | 5/1991 | Pless et al. .................................. 607/8 |
| 5,025,172 | 6/1991 | Carroll et al. . |
| 5,184,616 | 2/1993 | Weiss ........................................ 607/4 |
| 5,199,429 | 4/1993 | Kroll et al. . |
| 5,243,975 | 9/1993 | Alferness et al. ........................... 607/7 |
| 5,342,404 | 8/1994 | Alt et al. ................................... 607/6 |
| 5,366,484 | 11/1994 | Kroll ......................................... 607/5 |
| 5,421,830 | 6/1995 | Epstein et al. ............................. 607/30 |
| 5,509,927 | 4/1996 | Epstein et al. ............................. 607/32 |
| 5,531,764 | 7/1996 | Adams et al. .............................. 607/5 |

OTHER PUBLICATIONS

Ultrahigh-Energy Hydrogen Thyratron/SCR Bidirectional Waveform Defibrillator. J. C. Schuder, J. H. Gold and W. C. McDaniel, Medical & Biological Engineering & Computing, Jul. 1982 pp. 419–424.

*Primary Examiner*—Jeffrey R. Jastrzab
*Attorney, Agent, or Firm*—Curtis G. Rose

[57] ABSTRACT

A defibrillator applies a defibrillation waveform to a patient. Waveform selection circuitry in the defibrillator uses a reference waveform to give the defibrillation waveform a desired shape. Preferably, a user selects between a plurality of stored waveforms, and the reference waveform is generated from the stored waveform selected by the user. As an alternative to selecting a stored waveform, the user may also create a new waveform, which is then stored for a future selection.

20 Claims, 6 Drawing Sheets

5,725,560

1

DEFIBRILLATOR WITH WAVEFORM SELECTION CIRCUITRY

FIELD OF THE INVENTION

This invention relates to defibrillators. More specifically, this invention relates to defibrillators with waveform selection circuitry.

BACKGROUND OF THE INVENTION

Cardiac defibrillators are used to apply electrical energy to patients to restore a sinus rhythm to fibrillating hearts. One class of conventional defibrillators applies this electrical energy in the form of a damped sinusoidal waveform. Another class of conventional defibrillators applies this electrical energy in the form of a truncated exponential waveform. Both of these classes of conventional defibrillators create these respective waveforms by discharging a capacitor into a pulse forming circuit made of passive components such as resistors, capacitors, and inductors.

While conventional defibrillators have reliably produced damped sinusoidal and truncated exponential waveforms for years, recent studies have brought into question whether these waveforms are the best waveforms for defibrillating a heart. These studies have conducted experiments with other waveforms to determine if any of these waveforms would do a better job at defibrillating a heart. While these studies are as of yet inconclusive, it remains quite possible that there are not one but several optimal waveforms, depending on the circumstances in when/how a defibrillator is used (emergency, open heart surgery, multiple shocks, etc.), and some or perhaps even all of these optimal waveforms have yet to be discovered. Unfortunately, since a conventional defibrillator is restricted to using the single waveform it can produce (perhaps in a choice of waveform amplitudes, but in only one waveform shape), some patient's hearts are unable to be successfully defibrillated, perhaps solely for the simple reason that an ineffective defibrillation waveform was used in their particular case.

SUMMARY OF THE INVENTION

A defibrillator applies a defibrillation waveform to a patient. Waveform selection circuitry in the defibrillator uses a reference waveform to give the defibrillation waveform a desired shape. Preferably, a user selects between a plurality of stored waveforms, and the reference waveform is generated from the stored waveform selected by the user. As an alternative to selecting a stored waveform, the user may also create a new waveform, which is then stored for a future selection.

2

Figure 6:
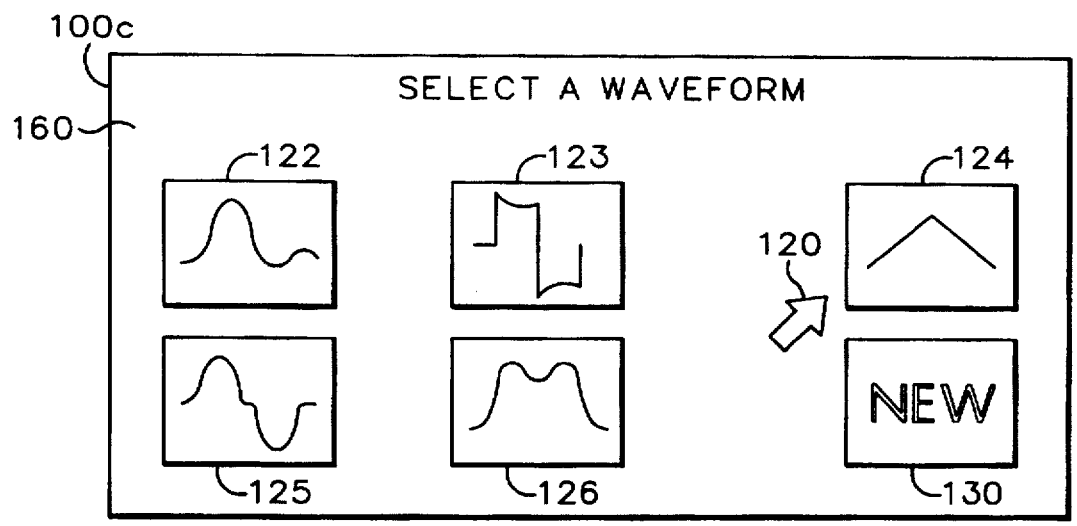
FIG. 6 shows a user interface for selecting a stored waveform in yet another embodiment of the invention.
Figure 7:
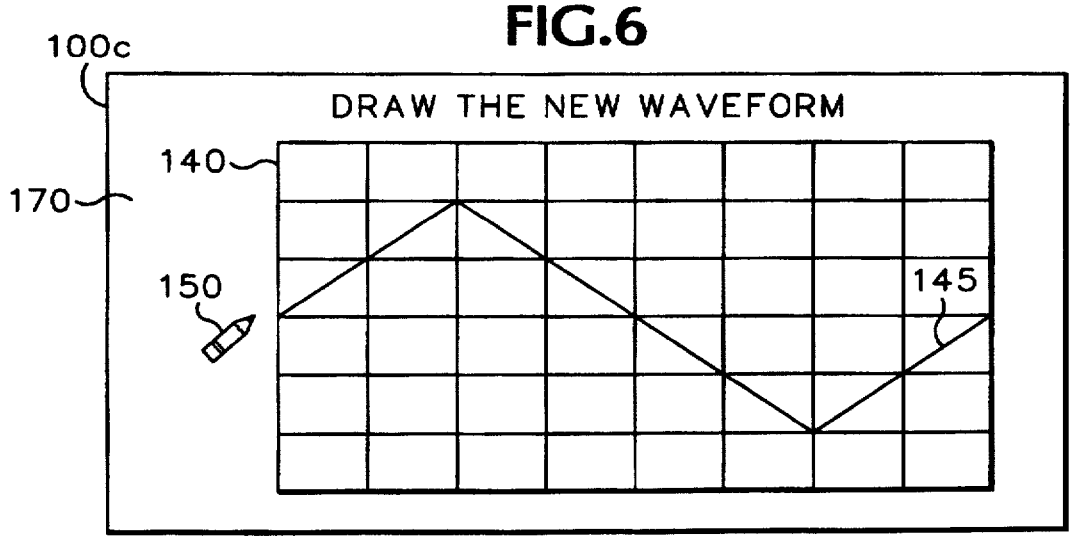

FIG. 7 shows how a user creates a new waveform using the user interface of FIG. 6.

Figure 8:
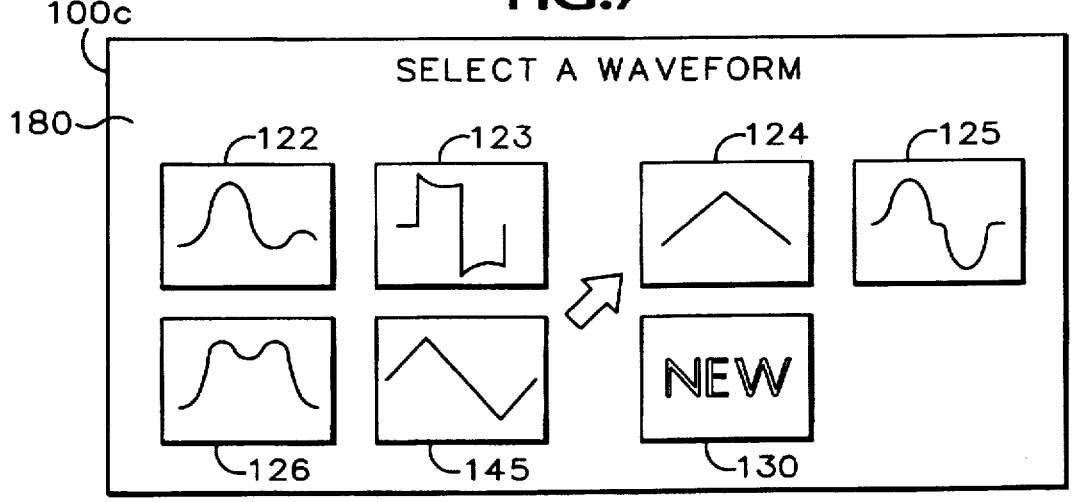

FIG. 8 shows the user interface of FIG. 6, updated to include the new waveform created in FIG. 7.

Figure 9:
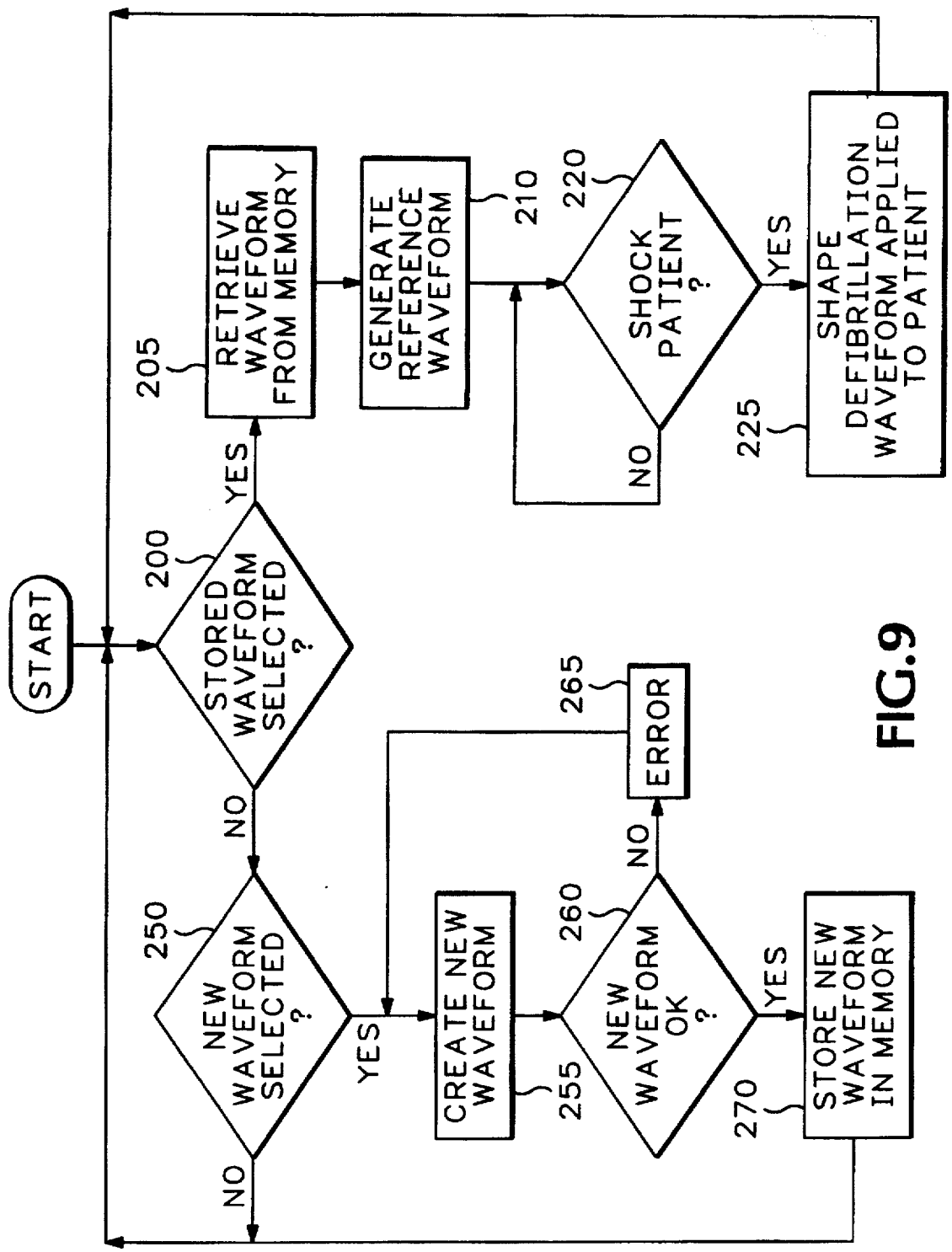

FIG. 9 shows the flowchart of the preferred embodiment of the invention.

DETAILED DESCRIPTION OF THE PREFERRED AND ALTERNATE EMBODIMENTS

Figure 1:
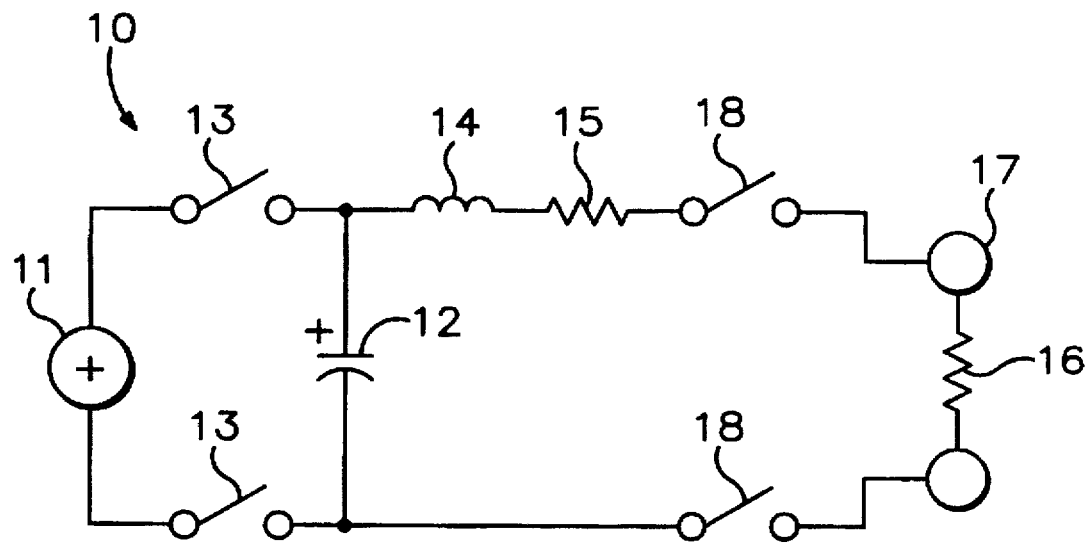
FIG. 1 is a conventional defibrillator.
Figure 5:
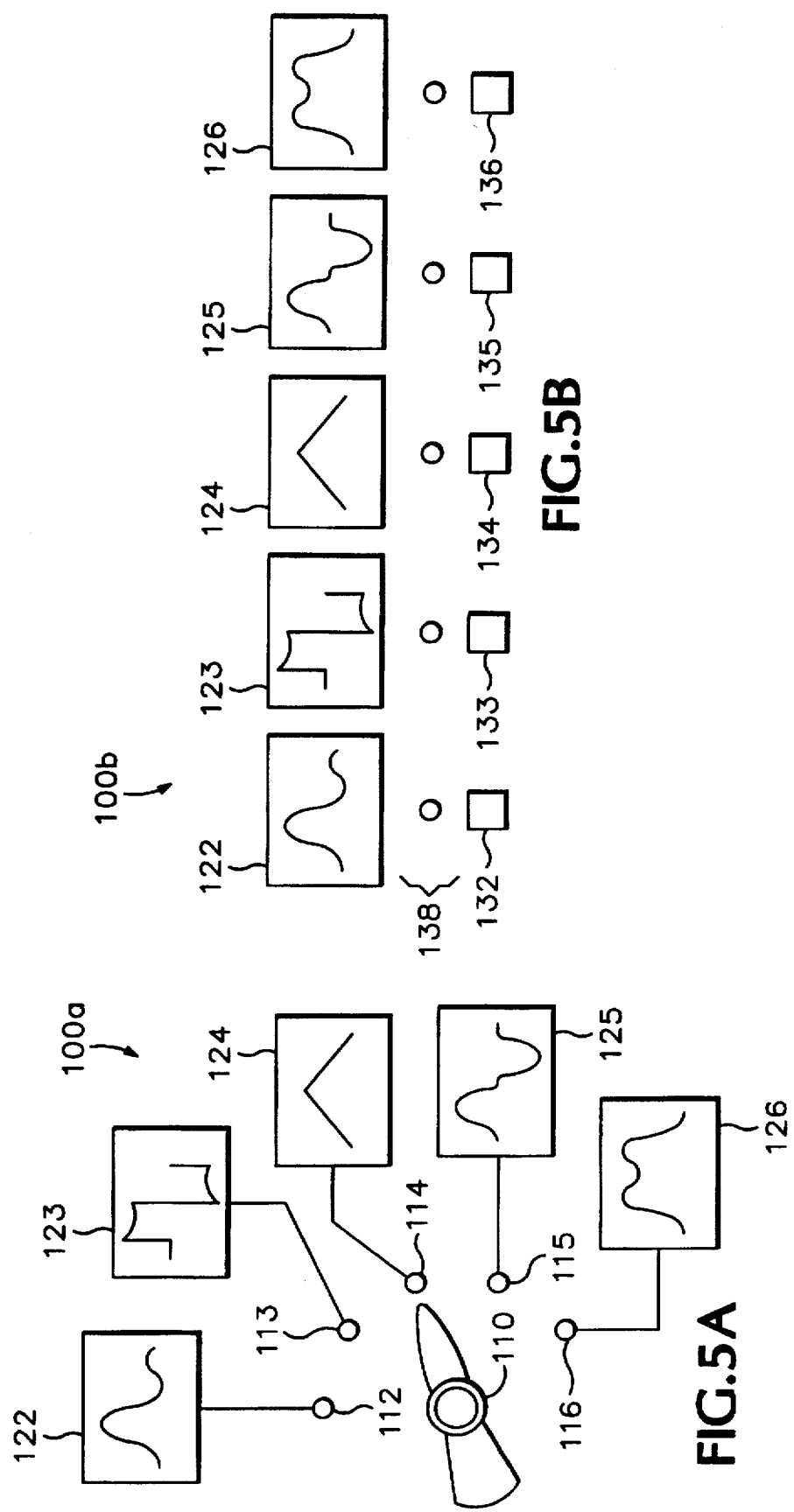
FIG. 5A shows a user interface for selecting a stored waveform of one embodiment of the invention.
FIG. 5B shows a user interface for selecting a stored waveform in another embodiment of the invention.

FIG. 1 shows a conventional defibrillator 10. Capacitor 12 is charged by power supply 11 when switches 13 are closed. An electrical path is formed from the positive terminal of capacitor 12, through inductor 14 and resistor 15, through defibrillator pads or contacts 17 to a patient 16 represented by a resistor, and to the other terminal of capacitor 12. The path is broken by switches 18. This circuit applies energy to patient 16 in the form of a damped sinusoidal waveform (shown as waveform 122 of FIG. 5A).

Figure 2:
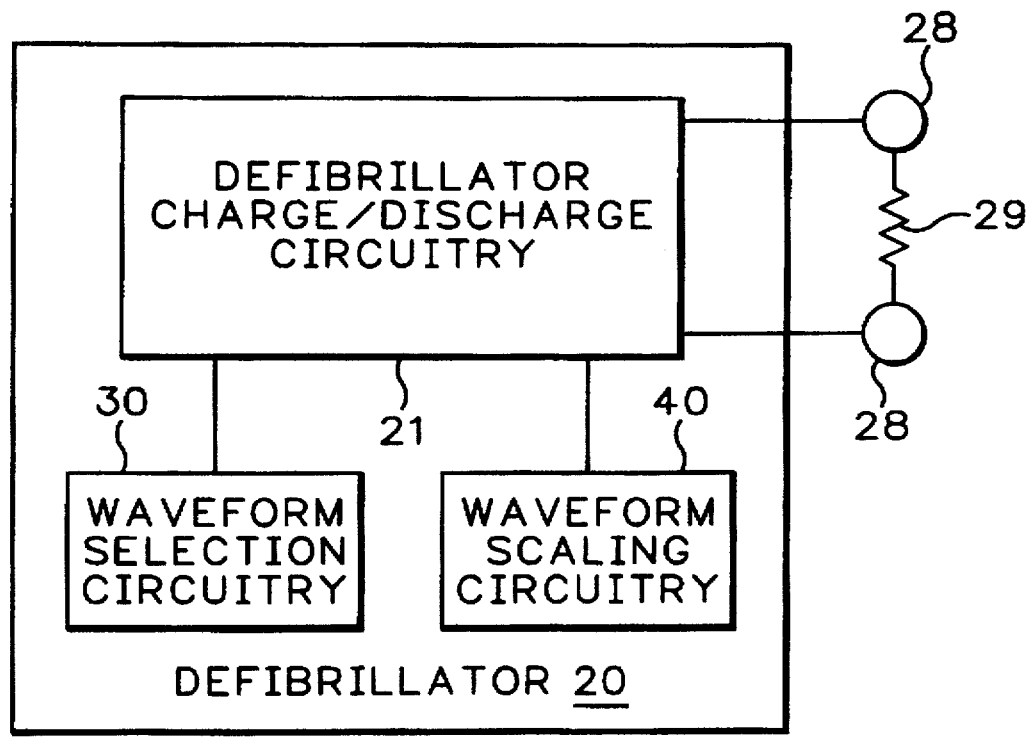
FIG. 2 is a high level block diagram of the defibrillator of one embodiment of the invention.

FIG. 2 is a high level block diagram of defibrillator 20 of one embodiment of the invention. Defibrillator 20 contains defibrillator charge/discharge circuitry 21 connected to waveform selection circuitry 30 and waveform scaling circuitry 40. Defibrillator charge/discharge circuitry 21 is also connected to defibrillator pads or contacts 28, which are placed on patient 29.

Figure 3:
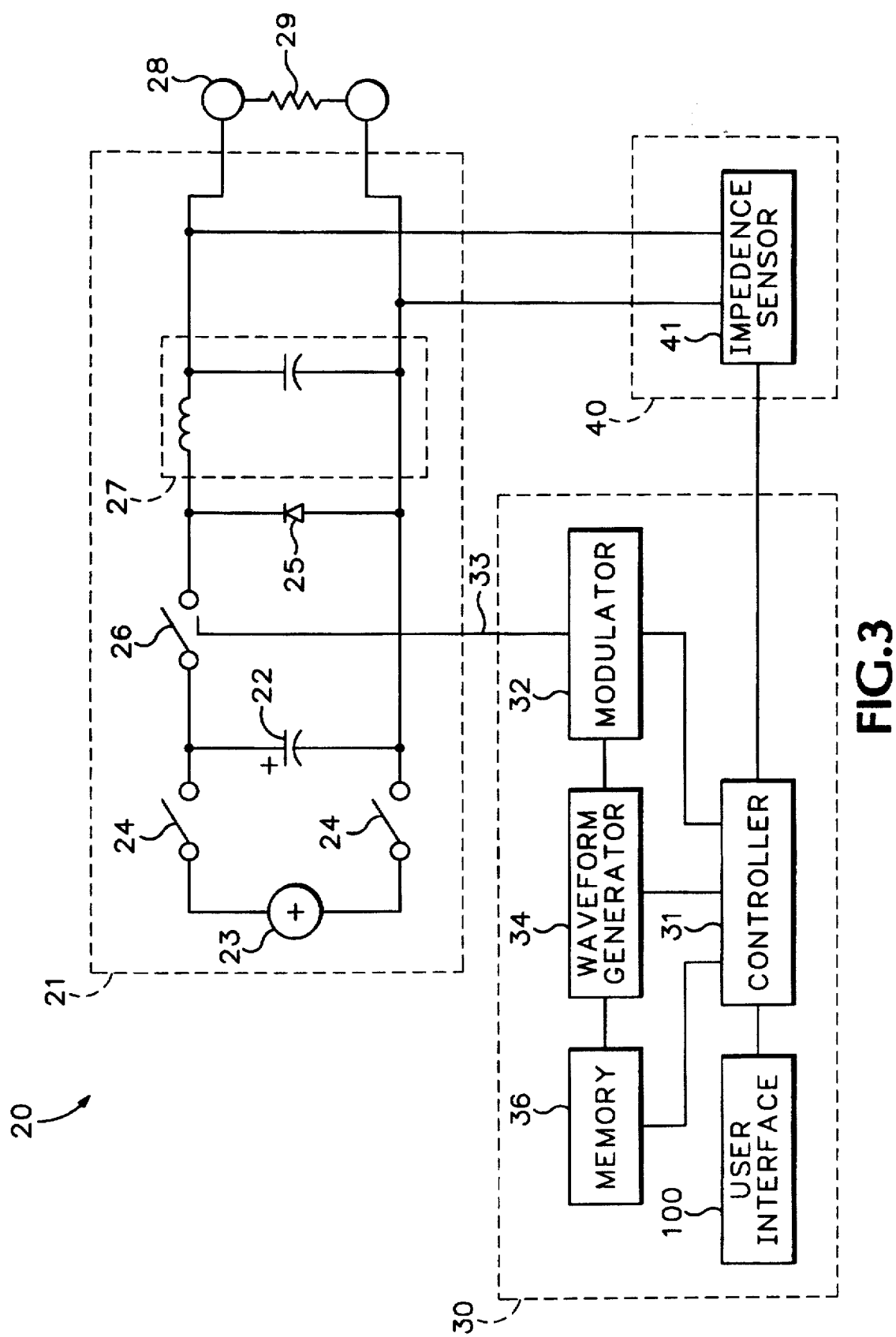
FIG. 3 is a detailed view of the defibrillator of FIG. 2.

FIG. 3 shows defibrillator 20 in more detail. Defibrillator charge/discharge circuitry 21 includes a capacitor or other energy storage device 22, which is charged via battery or other power source 23 when switches 24 are closed. Switch 26 is opened and closed rapidly by modulator 32 of waveform selection circuitry 30 to shape the defibrillator waveform applied to the patient by using the reference waveform, in a manner that will be explained in more detail later. This defibrillator waveform can be characterized in terms of current, voltage, instantaneous power, or total energy.

Defibrillator charge/discharge circuitry 21 further includes a low-pass filter circuit 27 connected between electronic switch 26 and patient impedance 29. Filter circuit 27 is designed to smooth the defibrillation energy waveform applied to the patient by removing high-frequency components introduced by switching electronic switch 26. In the preferred embodiment, switch 26 is an insulated-gate bipolar transistor (IGBT), although other switches could be used. In the embodiment shown, filter 27 comprises an inductor connected in series with defibrillation contacts 28 and a capacitor connected in parallel with patient impedance 29. A commutating diode 25 is also connected in parallel with patient impedance 29 on the unfiltered side of filter 27.

Waveform selection circuitry 30 includes controller 31 connected to memory 36, waveform generator 34, modulator 32, and user interface 100. Controller 31 is suitably programmed to execute the flowchart of FIG. 9, as will be discussed in more detail later. Memory 36 stores one or more waveforms, referred to herein as stored waveforms. Each stored waveform preferably comprises a sequence of digital numeric amplitude values, with successive values representing amplitudes of a waveform at successive points in time. Alternatively, one or more stored waveforms can be represented as one or more mathematical equations, such as A sin x, (where A is the amplitude, and where x is from 0–π for a monophasic waveform, and from 0–2 π for a biphasic waveform), or in some other format understandable by waveform generator 34. Any information stored in memory 36 that is used to give the defibrillation waveform a desired shape is considered a "stored waveform" and falls within the spirit and scope of the invention. Memory 36 is preferably non-volatile random access memory, but could be a ROM, a hard drive, or other forms of storage.

Waveform generator 34 uses a stored waveform from memory 36 to generate a reference waveform. Waveform generator 34 is preferably a digital to analog converter that converts the digital information contained in the stored waveform into an analog reference waveform having a predetermined amplitude and period, although other circuitry and/or software could be used.

An alternate embodiment has been contemplated where the information contained in memory 36 is used directly by the defibrillator to give the defibrillation waveform a desired shape. In this embodiment, the stored waveform is the same as the reference waveform, and the stored waveform from memory 36 is input directly into modulator 32, with waveform generator 34 no longer being necessary.

In the preferred embodiment, modulator 32 is a pulse width modulator, although it could modulate frequency or phase, or perform some other type of function that controls switch 26 in a manner that gives the defibrillation waveform a desired shape. Modulator 32, using the reference waveform generated by waveform generator 34 as an input, rapidly opens and closes switch 26 over low voltage signal line 33. This action gives the high voltage defibrillation waveform applied to the patient a shape like the reference waveform.

Preferably, predictive control is used to scale the applied defibrillation waveform. Predictive control involves measuring patient impedance just prior to defibrillation via impedance sensor 41, and scaling the applied defibrillation waveform in accordance with the measured impedance. Commonly assigned U.S. Pat. No. 4,840,177, issued Jun. 20, 1989, hereby incorporated by reference, describes one method of predictive control in some detail. When using predictive control, reference waveform transmitted on signal line 33 is scaled by a factor that is determined prior to defibrillation based on the measured impedance of patient 29 between defibrillation paddles 28.

As mentioned previously, waveform selection circuitry 30 enables a user to select between a plurality of stored waveforms prior to defibrillation. User interface 100 allows the user to make this selection. FIGS. 5A, 5B and 6 show three embodiments of user interface 100, referred to herein as interfaces 100a, 100b, and 100c, respectively. Those skilled in the art will appreciate that these interfaces are exemplary of a wide variety of possible user interfaces that could be used and still fall within the spirit and scope of the invention. Referring now to FIG. 5A. Interface 100a contains multi-positional switch 110, and switch contacts 112–116. Switch contacts 112–116 correspond to stored waveforms 122–126. A user selects a stored waveform by moving multi-positional switch 110 to its corresponding switch contact position. For example, if a user moves multi-positional switch 110 to switch contact position 112, he is selecting stored waveform 122.

FIG. 5B shows interface 100b, another embodiment of user interface 100. In this embodiment, buttons 132–136 correspond to stored waveforms 122–126. The user selects a stored waveform by pressing the corresponding button. When the corresponding button is pressed, the indicator light 138 directly above the corresponding button illuminates.

FIG. 6 shows interface 100c, another embodiment of user interface 100. In this embodiment, screen 160 displays graphical representations of stored waveforms 122–126. The user selects a stored waveform by moving cursor 120 over the top of a stored waveform and clicking a mouse button or performing some other type of action.

The embodiment shown in FIG. 6 also allows a user to create a new waveform. If a user selects new waveform box 130, screen 170 (FIG. 7) is displayed. Screen 170 allows the user to draw a new waveform using a wave shape building tool, such as BenchLink ARB, manufactured by the Hewlett-Packard Company, or a general purpose drawing tool, such as Microsoft Draw, manufactured by the Microsoft Corporation, or the like. The user takes pencil icon 150 and draws the new waveform, such as new waveform 145. After the waveform is created, a screen such as screen 180 (FIG. 8) is displayed. Note that screen 180 is the same as screen 160, except that new waveform 145 is now a stored waveform displayed for selection.

As stated previously, controller 31 (FIG. 3) is suitably programmed to execute the flowchart of FIG. 9. Referring now to FIG. 9, block 200 checks to see if a stored waveform has been selected. This selection can be made by any of the user interfaces shown in FIGS. 5A, 5B or 6, or by one of the embodiments described below, or by another method appreciated by those readers skilled in the art.

One embodiment has been contemplated where only one waveform is stored in memory 36. In this embodiment, block 200 automatically selects this stored waveform.

Another embodiment has been contemplated where this selection is made automatically based on an analysis of patient information, such as the patient's ECG waveform indicating a shockable arrhythmia, respiratory factors, cardiac output, ECG frequency content, etc. This patient information is received via defibrillator contacts 28, separate ECG electrodes, and/or other probes/input devices. The ECG waveform can take on well known characteristics which can be used to classify the ECG waveform as normal sinus rhythm, or into one of several different types of arrhythmias, such as ventricular tachycardia, ventricular fibrillation, asystole, etc. Since arrhythmias often degenerate (i.e. need defibrillation, and become increasingly more difficult to correct with a defibrillator) over time, different defibrillator waveforms may be indicated for different arrhythmias detected on the ECG waveform. In this embodiment, block 200 selects a stored waveform that is determined to be best able to correct the particular type of arrhythmia contained on the ECG waveform.

If a stored waveform has been selected, either by the user using one of the user interfaces shown in FIGS. 5A, 5B or 6, or automatically in the embodiments discussed above, block 200 is answered affirmatively, and block 205 retrieves the selected waveform from memory 36 (FIG. 3). Block 210 uses waveform generator 34 (FIG. 3) to generate the reference waveform. Block 220 then checks to see if an indication has been received to shock the patient. This indication can either be by the user performing a specific action, such as actuating switches on defibrillator pads 28, or automatically based on an analysis of patient information, such as the patient's ECG waveform indicating a shockable arrhythmia, respiratory factors, cardiac output, ECG frequency content, etc. In either event, when block 220 is answered affirmatively, block 225 instructs modulator 32 (FIG. 3) to use the reference waveform generated by waveform generator 34 to shape the defibrillator waveform by rapidly opening and closing switch 26 (FIG. 3). Flow of control loops back to block 200 to wait for a stored or new waveform to be selected.

Referring again to FIG. 9, if block 200 determines that a stored waveform has not been selected, block 250 asks if a new waveform has been selected, such as by the selection of new waveform box 130 in FIG. 6. If not, flow of control loops back to block 200 to wait for either a stored or a new waveform to be selected. If a new waveform has been selected, block 255 creates the new waveform, by, for example, allowing the user to draw one, as is shown in FIG. 7. Block 260 checks the new waveform to see if it can be successfully used by modulator 32 to shape the defibrillator waveform. Waveforms that are too complex for modulator 32 to use are rejected by block 260, and an error message is posted in block 265. If block 260 determines that the new waveform is acceptable, block 270 stores it in memory 36, and flow of control loops back to block 200 to wait for a stored or new waveform to be selected.

Figure 4:
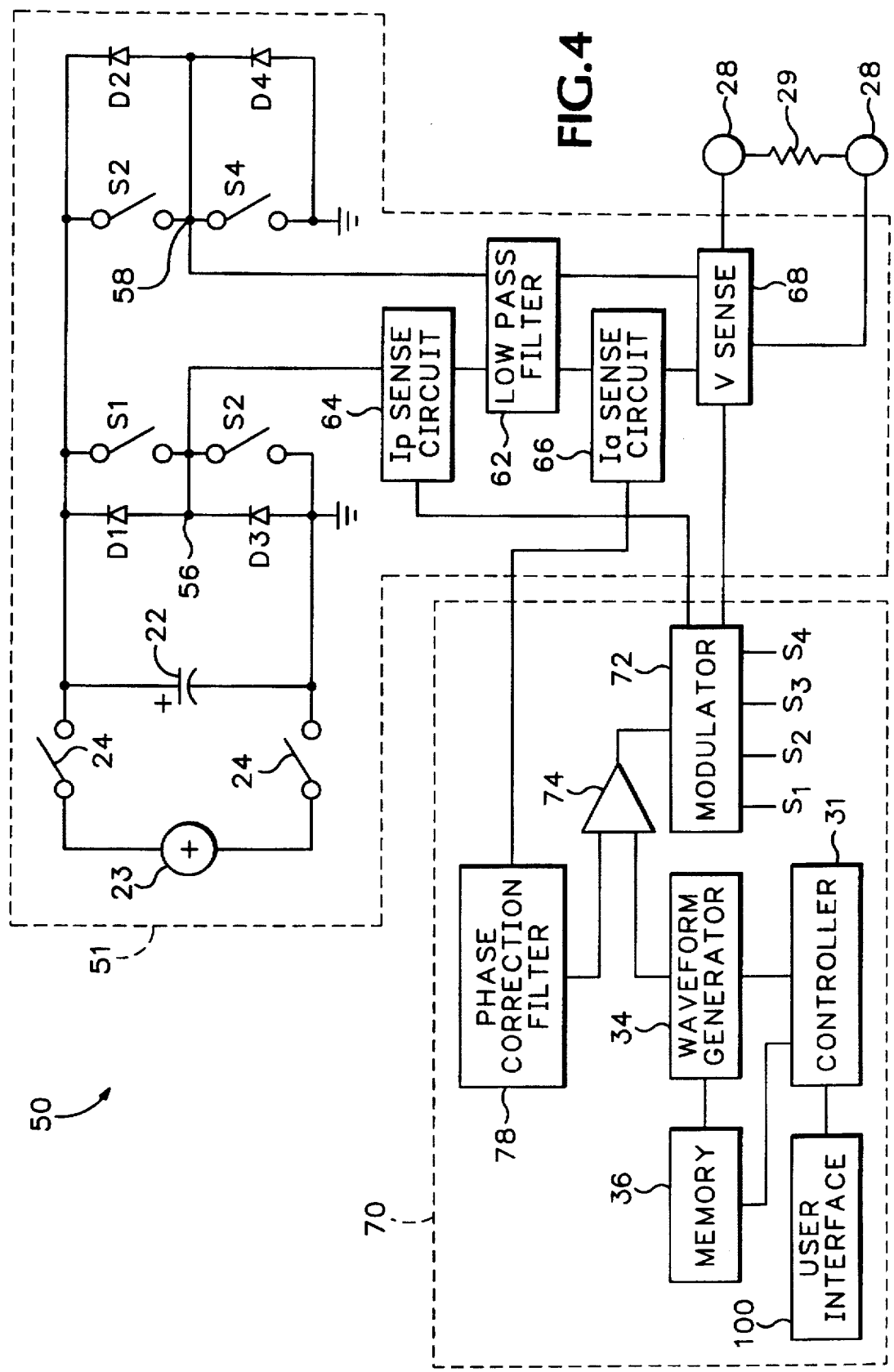
FIG. 4 is a detailed view of the defibrillator of another embodiment of the invention.

Referring again to FIGS. 5–8, note that some of the stored waveforms 122–126 are monophasic, while others are biphasic. While user interface 100 is used with both defibrillator embodiments (previously discussed defibrillator 20 of FIG. 3 and soon to be discussed defibrillator 50 of FIG. 4), only defibrillator 50 of FIG. 4 is capable of using a defibrillator waveform that is biphasic. Therefore, if user interface 100 is used in defibrillator 20 of FIG. 3, only monophasic stored waveforms 122, 124, and 126 would be capable of being selected, and any new waveforms created would also be monophasic.

FIG. 4 shows defibrillator 50 in accordance with another embodiment of the invention. Defibrillator 50 uses closed-loop pulse-width modulation techniques to regulate the defibrillation energy applied to a patient instead of predictive control used in defibrillator 20. Defibrillator 50 also has the capability to generate biphasic waveforms. Defibrillator 50 contains defibrillator charge/discharge circuitry 51 and waveform selection circuitry 70.

Like defibrillator 20, defibrillator 50 includes capacitor 22 charged by battery or charging device 23 when switches 24 are activated. Also like defibrillator 20, the patient is represented by resistance 29. A pair of defibrillator contacts or paddles 28 is also shown.

Energy application is controlled by a pulse-width modulation switching network operatively connected between the capacitor 22 and defibrillator contacts 28. In the embodiment of FIG. 4, the switching network comprises an H-bridge converter, including four electronic switches S1, S2, S3, and S4. Switches S1 and S3 are connected in series between the positive and negative terminals of capacitor 22. A first intermediate switched node 56 is defined between switches S1 and S3. Switches S2 and S4 are likewise connected between the positive and negative terminals of capacitor 22. A second intermediate switched node 58 is defined between switches S2 and S4. Commuting diodes D1, D2, D3, and D4 are connected with each of switches S1, S2, S3, and S4, respectively, as shown. Defibrillator contacts 28 are electrically connected between first and second switched nodes 56 and 58, respectively, in conjunction with intervening feedback and filter circuits that will be described in more detail below. During defibrillation, patient impedance 29 is electrically connected in series between switched nodes 56 and 58. As will be described in more detail below, switches S1 and S4 are active (rapidly switched on and off by modulator 72) during positive portions of the reference waveform, while switches S2 and S3 are off. Likewise, switches S2 and S3 are active (rapidly switched on and off by modulator 72) during negative portions of the reference waveform, while switches S1 and S4 are off.

To smooth the resulting defibrillator waveform, defibrillator charge/discharge circuitry 51 of defibrillator 50 includes a low-pass filter 62, connected between switched nodes 56 and 58 and patient impedance 29. In the preferred embodiment, the low-pass filter comprises an inductance in series with each defibrillator contact and a capacitor connected in parallel with patient impedance 29.

Defibrillator charge/discharge circuitry 51 also includes several components for sensing various characteristics of the defibrillation energy waveform actually applied to a patient. For instance, defibrillator charge/discharge circuitry 51 includes peak current detection circuit 64, preferably a low-value resistor or a current transformer, connected in series with defibrillation contacts 28 on the unfiltered side of lowpass filter 62. Another current detection circuit 66 is connected in series with patient impedance 29 on the filtered or patient side of lowpass filter 62 to measure average current applied to the patient. Voltage detection circuit 68 is also connected on the filtered or patient side of lowpass filter 62, in parallel with patient impedance 29.

Waveform selection circuitry 70 of defibrillator 50 shares many similarities with waveform selection circuitry 30 of defibrillator 20 of FIG. 3, including controller 31, waveform generator 34, memory 36, and user interface 100. Modulator 72 is slightly more complex than modulator 32 of FIG. 3, since it must control four switches instead of just one. In this embodiment of the invention, modulator 72 is configured to act as a switch-mode power conversion circuit having H-bridge switch control outputs connected to control the on/off state of switches S1, S2, S3, and S4, respectively. Switches S1, S2, S3, and S4 are preferably insulated-gate bipolar transistors, commonly referred to as IGBTs.

The output line from waveform generator 34 is connected to a first input of differencing block 74. A second input of differencing block 74 is connected to receive a signal representing the actual current being applied to the patient. This signal is derived from average current detection circuit 66 by passing the output of average current detection circuit 66 through a phase correction filter 78. The output signal of differencing block 74, an error signal, is input into modulator 72. This error signal provides feedback into modulator 72, so that the actual defibrillator waveform can be regulated to more accurately correspond to the desired defibrillator waveform. While current feedback is used in this embodiment, voltage feedback, or a combination of current and voltage feedback, could also be used.

In this embodiment, modulator 72 uses the peak current and voltage measurements to detect situations in which defibrillation should be aborted. A peak current signal, produced by peak current detection circuit 64, is connected to an input of modulator 72. A voltage signal, produced by voltage circuit 68, is connected to another input of modulator 72. Modulator 72 is configured to open all switches S1, S2, S3, and S4 in response to an overvoltage or overcurrent condition.

In the embodiment shown in FIG. 4, modulator 72, controller 31, waveform generator 34, differencing block 74, and phase correction filter 78 are preferably implemented within a digital signal processor (DSP), although discrete components could also be used. Use of a DSP provides for a great degree of flexibility, efficiency, and processing accuracy.

A variety of energy conversion circuits can be used in place of the illustrated H-bridge converter. For instance, a half-bridge converter might be suitable in some cases. Alternatively, buck or boost mode converters, multiple converters, or multiple capacitors might also be used.

I claim:

1. A defibrillator comprising:

memory;

an energy storage device;

defibrillator contacts for applying a defibrillation waveform to a patient from the energy storage device;

a switch, operatively coupled between said energy storage device and said defibrillator contacts;

waveform selection circuitry for generating a reference waveform, a modulator using said reference waveform as an input to control said switch to give said defibrillation waveform a desired shape;

a user interface to allow a user to select a selected waveform from a plurality of waveforms stored in memory, wherein said reference waveform is generated from said selected waveform by said waveform selection circuitry; and wherein said user interface also allows said user to draw a new waveform on a display screen and store said new waveform as one of a plurality of waveforms stored in memory.

2. The defibrillator of claim 1, wherein said user interface is a multi-positional switch.

3. The defibrillator of claim 1, wherein said user interface is a screen displayed to a user.

4. The defibrillator of claim 1, wherein said user interface is a plurality of buttons selectable by a user.

5. The defibrillator of claim 1, wherein said waveform selection circuitry automatically selects a selected waveform from a plurality of waveforms stored in memory, and wherein said reference waveform is generated from said selected waveform by said waveform selection circuitry.

6. The defibrillator of claim 5, further comprising:

means for analyzing patient information;

said automatic selection of said stored waveform is responsive to said means for analyzing patient information.

7. The defibrillator of claim 1, further comprising:

waveform scaling circuitry for measuring patient impedance and scaling said defibrillation waveform in accordance with said patient impedance.

8. The defibrillator of claim 1, further comprising: a differencing block having a first input connected to said waveform selection circuitry, a second input adapted to be coupled to a patient, and an output which provides feedback to said waveform selection circuitry to regulate said defibrillation waveform.

9. The defibrillator of claim 1, wherein said energy storage device is a capacitor.

10. The waveform selection circuitry of claim 1, further comprising:

a controller;

memory, connected to said controller;

a waveform generator, connected to said controller;

a user interface, connected to said controller; and said modulator, connected to said controller.

said user interface usable by a user to select a stored waveform out of memory, said waveform generator generating a reference waveform from said stored waveform, said modulator using said reference waveform as an input to rapidly open and close said switch to give said defibrillation waveform said desired shape.

11. A method of applying a defibrillation waveform to a patient, comprising the steps of:

selecting a selected waveform from a plurality of waveforms stored in memory;

generating a reference waveform from the selected waveform;

shaping the defibrillation waveform as a function of the reference waveform; and applying the defibrillation waveform to the patient;

wherein said selecting a selected waveform step further comprises the steps of:

choosing an option to create a new waveform;

drawing a new waveform on a display screen;

saving said new waveform; and selecting said new waveform as said selected waveform.

12. The method of claim 11, wherein said selecting a selected waveform step further comprises the step of:

moving a multi-positional switch to a first position corresponding to a first stored waveform.

13. The method of claim 11, wherein said selecting a selected waveform step further comprises the step of:

selecting a button corresponding to a first stored waveform.

14. The method of claim 11, wherein said selecting a selected waveform step further comprises the steps of:

moving a cursor over a graphical representation of a first stored waveform displayed on a display screen; and clicking a mouse button while said cursor is over said graphical representation of said first stored waveform displayed on said display screen.

15. The method of claim 11, wherein said selecting step is done automatically.

16. The method of claim 15, further comprising the step of:

analyzing patient information;

wherein said selecting step is responsive to the step of analyzing patient information.

17. The method of claim 16, wherein said step of analyzing patient information further comprises the steps of:

analyzing an ECG waveform;

identifying a type of arrhythmia; and selecting said selected waveform based on said type of arrhythmia identified in said identifying step.

18. The method of claim 11, further comprising the steps of:

measuring the impedance of said patient; and scaling said defibrillation waveform in accordance with said patient impedance.

19. The method of claim 11, further comprising the step of:

using feedback to regulate said defibrillation waveform.

20. A defibrillator, comprising:
a charge/discharge circuit, further comprising:
    an energy storage device;
    defibrillator contacts for applying a defibrillation waveform to a patient from the energy storage device;
    a switch, operatively coupled between said energy storage device and said defibrillator contacts;
waveform selection circuitry, further comprising:
    a controller;
    memory, connected to said controller;
    a waveform generator, connected to said controller;
    a user interface, connected to said controller;
    a modulator, connected to said controller,
said user interface usable by a user to select a stored waveform out of memory, said waveform generator generating a reference waveform from said stored waveform, said modulator using said reference waveform as an input to rapidly open and close said switch to give said defibrillation waveform a desired shape, and
wherein said user interface also allows said user to draw a new waveform on a display screen and store said new waveform as one of a plurality of stored waveforms.

* * * * *